(12) United States Patent
Ihns

(10) Patent No.: US 11,932,413 B2
(45) Date of Patent: *Mar. 19, 2024

(54) COCKPIT PRESSURIZATION AND OXYGEN WARNING SYSTEM

(71) Applicant: Avalex Technologies LLC, Gulf Breeze, FL (US)

(72) Inventor: Jurgen R. Ihns, Gulf Breeze, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/851,768

(22) Filed: Jun. 28, 2022

(65) Prior Publication Data

US 2022/0348349 A1 Nov. 3, 2022

Related U.S. Application Data

(60) Division of application No. 16/816,736, filed on Mar. 12, 2020, now Pat. No. 11,377,227, which is a continuation of application No. 16/006,178, filed on Jun. 12, 2018, now Pat. No. 10,640,230.

(60) Provisional application No. 62/652,581, filed on Apr. 4, 2018.

(51) Int. Cl.
*B64D 43/00* (2006.01)
*A61B 5/145* (2006.01)
*A61B 5/16* (2006.01)
*G01C 5/06* (2006.01)
*G01L 13/00* (2006.01)

(52) U.S. Cl.
CPC .......... *B64D 43/00* (2013.01); *A61B 5/14542* (2013.01); *A61B 5/16* (2013.01); *G01C 5/06* (2013.01); *G01L 13/00* (2013.01)

(58) Field of Classification Search
CPC ........ B64D 43/00; B64D 13/04; B64D 13/02; B64D 45/00; G01C 5/06; A61B 5/14542; A61B 5/16; A61B 5/18; G01L 13/00
USPC ......................................................... 340/970
See application file for complete search history.

(56) References Cited

U.S. PATENT DOCUMENTS

| | | | |
|---|---|---|---|
| 4,163,387 A * | 8/1979 | Schroeder ............. | G01L 9/0051 701/538 |
| 5,022,393 A * | 6/1991 | McGrady ................. | B64G 1/46 128/204.21 |
| 6,452,510 B1 * | 9/2002 | Zysko ..................... | B64D 25/00 701/4 |

(Continued)

*Primary Examiner* — Omar Casillashernandez
(74) *Attorney, Agent, or Firm* — Bryan W. Bockhop; Bockhop Intellectual Property Law, LLC

(57) ABSTRACT

A cockpit pressurization and oxygen warning system includes a cabin pressure input and an aircraft pressure input. A pilot interface includes a first visual indicator having a first recognizable characteristic disposed in a first position that is made visually perceptible when a first signal is asserted and a second visual indicator having a second recognizable characteristic esthetically different from the first recognizable characteristic and disposed in a second position different from the first position that is made visually perceptible when a second signal is asserted. A control circuit that is responsive to the cabin pressure input and the aircraft pressure input determines an acceptable range for the cabin altitude that corresponds to the aircraft altitude. The control circuit asserts the first signal when the cabin altitude is within the acceptable range and asserts the second signal when the cabin altitude is not within the acceptable range.

7 Claims, 7 Drawing Sheets

(56) References Cited

U.S. PATENT DOCUMENTS

| | | | | |
|---|---|---|---|---|
| 7,066,808 B2* | 6/2006 | Whitney | B64D 13/02 | 454/70 |
| 7,383,105 B2* | 6/2008 | Conroy, Jr. | B64D 13/00 | 701/5 |
| 7,633,409 B2* | 12/2009 | Naegler | B64D 13/04 | 340/945 |
| 7,670,214 B2* | 3/2010 | Conner | B64D 13/02 | 454/71 |
| 8,436,749 B2* | 5/2013 | Lillis | H05B 45/10 | 340/963 |
| 8,500,526 B2* | 8/2013 | Horner | B64D 13/04 | 454/76 |
| 9,242,725 B1* | 1/2016 | Lord | B64D 45/00 | |
| 10,352,084 B2* | 7/2019 | Hovel | E05F 15/70 | |
| 2003/0157875 A1* | 8/2003 | Horner | B64D 13/04 | 454/74 |
| 2004/0177745 A1* | 9/2004 | Kayama | G10H 1/0008 | 84/609 |
| 2005/0057377 A1* | 3/2005 | Naimer | G01C 23/00 | 340/978 |
| 2007/0271009 A1* | 11/2007 | Conroy | B64D 13/00 | 701/10 |
| 2012/0140125 A1* | 6/2012 | Pepitone | G02B 27/0149 | 348/800 |
| 2013/0120165 A1* | 5/2013 | McCollough | B64D 43/00 | 340/946 |
| 2015/0145702 A1* | 5/2015 | Waigl | B64C 1/1423 | 340/945 |
| 2015/0302671 A1* | 10/2015 | Sacle | G08G 5/0021 | 701/123 |
| 2016/0061680 A1* | 3/2016 | Knijnenburg | G01L 19/143 | 73/756 |
| 2016/0272341 A1* | 9/2016 | Van Horn | G08G 5/0021 | |
| 2017/0247112 A1* | 8/2017 | Horner | B64D 13/04 | |
| 2019/0054995 A1* | 2/2019 | Bredemeier | G08B 7/06 | |

* cited by examiner

Standard 20's

Standard 20's

Cabin High

Cabin Low

Oxygen Warn

Cabin Fluctuation

Standard 50's

Standard 50's

Standard 50's

Standard 100's

Standard 100's

Dual block 50's

BIT Warn

BIT Sensor

IBIT Progress

IBIT display patt

IBIT OK

60 Sec Hi / Low

60 Sec Diff

60 Sec Sched Graph

Schedule

OXY / ppO2*

60 Sec ppO2*

Oxygen PPO

Events

In Discrete status

Out Discrete status

Download

Download %

SW Update

Download %

Cal CPA

Cal complete

Clear Memory

Download %

Date / Time

Hours / cycles
FIG. 4AK
Cabin / Aircraft
Altitude
FIG. 4AL
OXY press
ppO2 value
FIG. 4AM
Memory
capacities
FIG. 4AN
Temperatures
FIG. 4AO
Volt / current
FIG. 4AP
5 VAC input
FIG. 4AQ
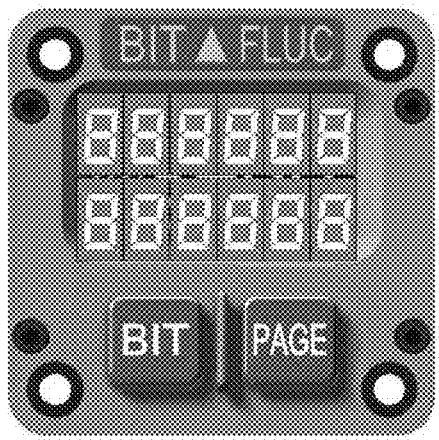
FIG. 5A
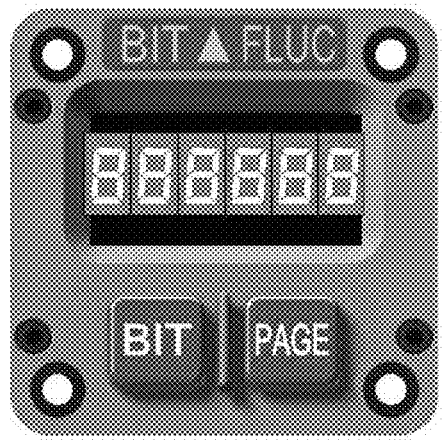
FIG. 5B

COCKPIT PRESSURIZATION AND OXYGEN WARNING SYSTEM

CROSS-REFERENCE TO RELATED APPLICATION(S)

This application claims the benefit of U.S. Provisional Patent Application Ser. No. 62/652,581, filed Apr. 4, 2018, the entirety of which is hereby incorporated herein by reference. This application is a continuation of U.S. patent application Ser. No. 16/006,178, filed Jun. 12, 2018, now patented as U.S. Pat. No. 10,640,230, the entirety of which is hereby incorporated herein by reference. This application is a divisional of U.S. patent application Ser. No. 16/816,736, filed Mar. 12, 2020, the entirety of which is hereby incorporated herein by reference.

BACKGROUND OF THE INVENTION

1. Field of the Invention

The present invention relates to avionics systems and, more specifically, to a system for warning when cockpit pressurization falls below a threshold.

2. Description of the Related Art

Aircraft cabin pressurization is typically controlled in advanced aircraft, such as fighter jets and commercial jets, using a constant differential mode, in which cabin pressure is maintained at a constant pressure difference between the air pressure inside the cabin and the ambient air pressure, regardless of aircraft altitude changes. The constant differential mode pressure differential is lower than the maximum differential pressure for which the airframe is designed, keeping the integrity of the pressure vessel intact.

In such advanced aircraft, pressurization becomes increasingly necessary at altitudes above 10,000 feet above sea level to protect the pilot from the risk of physiological problems caused by the low outside air pressure above that altitude. Such problems include hypoxia, altitude sickness, decompression sickness, and barotrauma. Hypoxia, results from reduced partial pressure of oxygen at high altitudes. Hypoxia reduces the alveolar oxygen tension in the lungs and subsequently in the brain, leading to diminished cognitive factors such as sluggish thinking, dimmed vision and loss of consciousness, which can result in fatal accidents if experienced by a pilot.

Some existing aircraft include instruments that indicate cabin altitude for monitoring pressurization. Cabin altitude is the hypothetical altitude corresponding to the pressure inside the cabin. For example, a pressurized aircraft flying at 40,000 feet above sea level (ASL) could be pressurized to a pressure corresponding to 8,000 feet ASL, which is the aircraft's cabin altitude. The pilot monitors the aircraft altitude and ensures that the cabin altitude maintains a correct differential according to a pressurization schedule for the aircraft.

However, advanced aircraft pilots are frequently stimulated by important events and such stimulation can result in the pilot being distracted from issues of pressurization. Also, pilots suffering from hypoxia can find it difficult to understand numerical digits displayed by monitoring instruments. As a result, they might have difficulty understanding existing pressurization monitoring instruments when the aircraft is experiencing pressure loss.

Therefore, there is a need for a pressurization warning system that presents pressurization indications in a format that is quickly comprehendible by individuals experiencing reduced cognitive ability as a result of hypoxia.

SUMMARY OF THE INVENTION

The disadvantages of the prior art are overcome by the present invention which, in one aspect, is a cockpit pressurization and oxygen warning system in an aircraft flown by a pilot and having an aircraft altitude and a cabin altitude. The system includes a cabin pressure input and an aircraft pressure input. A pilot interface includes a first visual indicator having a first recognizable characteristic disposed in a first position that is made visually perceptible when a first signal is asserted and a second visual indicator having a second recognizable characteristic esthetically different from the first recognizable characteristic and disposed in a second position different from the first position that is made visually perceptible when a second signal is asserted. A control circuit that is responsive to the cabin pressure input and the aircraft pressure input determines an acceptable range for the cabin altitude that corresponds to the aircraft altitude. The control circuit asserts the first signal when the cabin altitude is within the acceptable range and asserts the second signal when the cabin altitude is not within the acceptable range.

In another aspect, the invention is a cockpit pressurization monitoring apparatus that includes a cabin pressure input and an aircraft altitude input. A control circuit determines cabin altitude as a function of the cabin pressure input and determines an acceptable cabin altitude range as a function of the aircraft altitude. A pilot interface, responsive to the control circuit, includes a first light that illuminates with a first color when the cabin altitude is within the acceptable cabin altitude range and includes a second light, spaced apart from the first light, that illuminates with a second color, different from the first color, when the cabin altitude is outside of the acceptable cabin altitude range.

In yet another aspect, the invention is a method of presenting pressurization information to a pilot about an aircraft having an aircraft altitude and a cabin altitude, in which the aircraft altitude and the cabin altitude are sensed. It is determined if the cabin altitude is within an acceptable range given the aircraft altitude. When the cabin altitude is within an acceptable range, then a first indication is generated. When the cabin altitude is not within an acceptable range, then a second indication that is distinguishable from the first indication by the pilot when the pilot exhibits diminished cognitive factors associated with hypoxia is generated.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIGS. 5A-5B are depictions of two different screen formats employable with the present system.

DETAILED DESCRIPTION OF THE INVENTION

Figure 1:
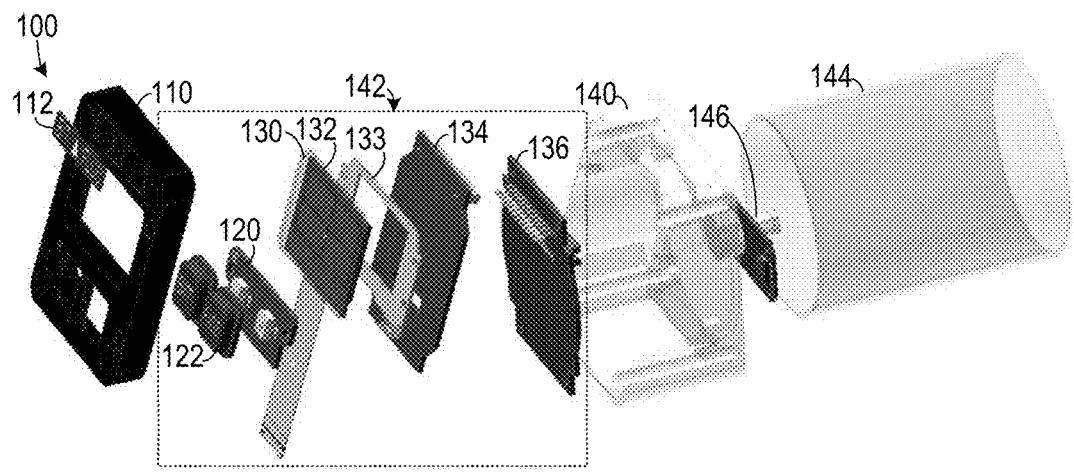
FIG. 1 is an exploded view of one embodiment of a cockpit pressurization and oxygen warning system.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

The present invention collects and presents information regarding the pressurization state of an aircraft's cockpit while in flight. Specifically, the invention detects cabin pressure and compares it to the aircraft pressure to determine the cabin altitude. If the cabin altitude is outside of a predetermined range, the invention presents an indication of such a situation in a way that is quickly perceptible by the pilot. The indication is also presented in a way that is more likely to be perceived by a pilot experiencing hypoxia-related sensory and cognitive factors. The quick and easily perceived indication of an abnormally low cabin altitude presented by the invention can be an important factor to a successful recovery from aircraft depressurization.

As shown in FIG. 1, one embodiment of a cockpit pressurization and oxygen warning system 100 for providing pressurization information to a pilot includes a back bezel 140 in which is disposed an electronics display suite 142 and which is capped by a front bezel 110. The electronics and display suite 142 includes an input button board 120 that incudes buttons used to receive pilot input, rubber key button covers 122 that protects the buttons, a display element 132 such as an organic light emitting diode (OLED) display for presenting visually perceptible information to the pilot, a filter glass 130 that protects the display element, a display bracket 133 for holding the display element 132 and providing electrical connections thereto, a front printed circuit board 134 that is electrically coupled to all display and input elements and upon which is mounted processor circuitry, and a back printed circuit board 136 that is electronically coupled to the front printed circuit board 134. An integrated pressure transducer 146 (such as the Honeywell IPT0020A33R sensor) is electrically coupled to the back printed circuit board 136 and senses cabin pressure. A rear can 142 protects the integrated pressure transducer 146 and any connections to the back printed circuit board 136. An indicator area overlay 112 can be placed in front of a portion of the display element 132 to present certain preselected messages by illuminating the portion of the display element 132 upon the occurrence of certain events.

Figure 2:
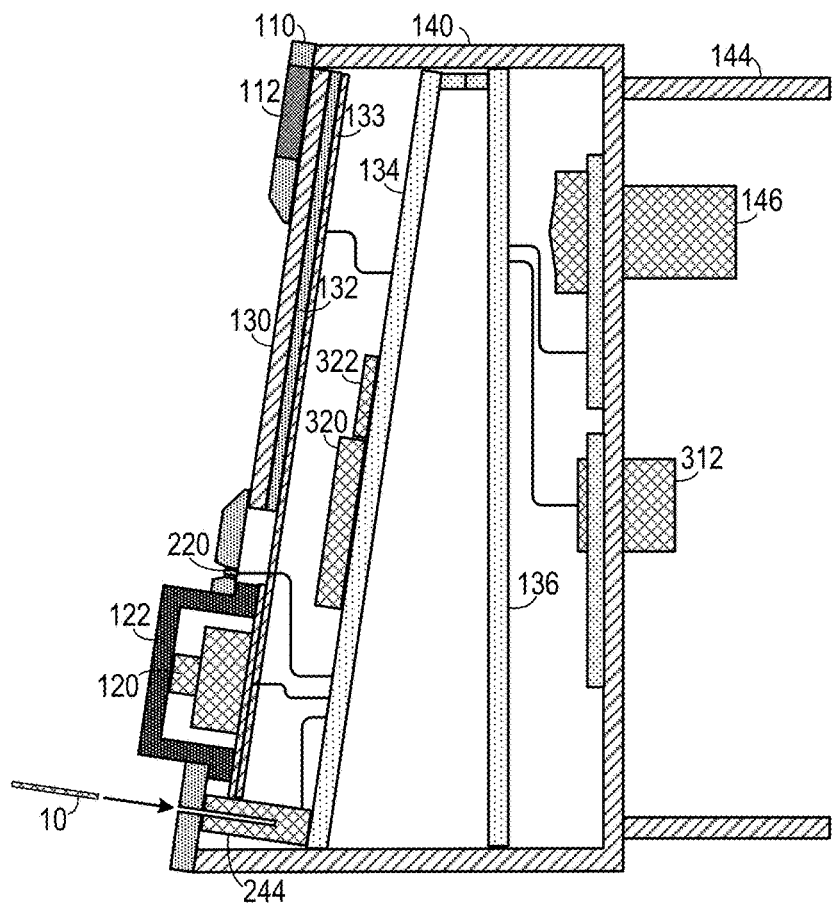
FIG. 2 is a cross sectional view of the system shown in FIG. 1.

As shown in FIG. 2, one embodiment employs a control circuit to manage and display the relevant data. The control circuit also generates a first signal when the cabin altitude is within the acceptable range and generates a second signal when the cabin altitude is not within the acceptable range. There first signal and the second signal used to control the outputs to the pilot. The control circuit can include a microprocessor 320 and a digital memory 322 coupled thereto. (As will be readily appreciated by those of skill in the art, other types of control circuits, such as microcontrollers, programmable logic arrays, analog control circuits and proprietary control circuits, etc. may be employed without departing from the scope of the invention.) The control circuit receives cabin pressure input from pressure transducer 146 and static pressure input from pressure transducer 312, and determines an acceptable range for the cabin altitude that corresponds to the aircraft altitude, which could be done by accessing a lookup table from the memory 322. A data card input 244 can be used in uploading and downloading data from a data card 10. The data can include software updates, data log information, diagnostic data, pilot preset preferences, etc. Such data card input 244 could include interfaces to devices such as: a flash memory card interface (e.g., an SD, XD or CF card interface), a USB port or one of the many other types of data interfaces known to the art.

Different states of the pilot interface 200 are shown in FIGS. 3A-3F. The pilot interface 200 includes: a display area 230 that presents various information about the pressurization state of the aircraft, a test button 240 that allows the pilot to run a self-test on the system, a page (or mode) button 242 that allows the pilot to change display modes manually, an indicator area 112 that presents certain fixed indicators, a situation-normal LED indicator 220 that indicates when cabin altitude is within a desirable range.

Figure 3A:
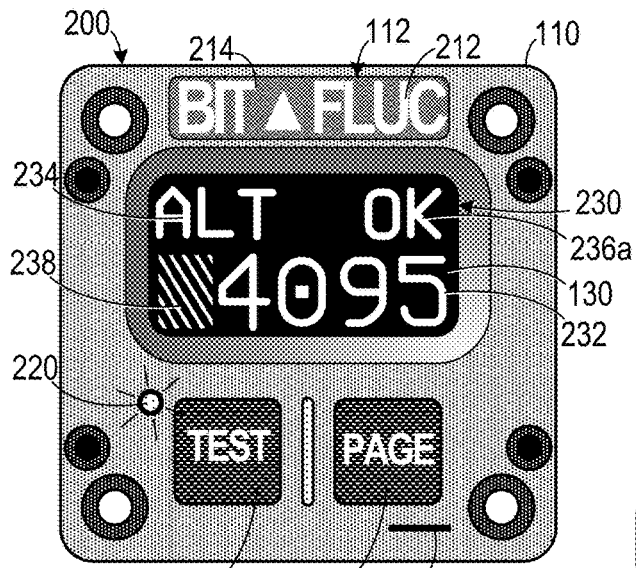
FIG. 3A-3F are schematic diagrams of a pilot interface employed in the system shown in FIG. 1 showing the interface during different cabin altitude states.

When the pilot depresses the page button 242 a mode signal is asserted and sensed by the control circuit, which causes the electronic display to cycle to a display mode selected from a plurality of display modes. In one of the display modes, an interface 200 that would be typical for a normally pressurized cabin is shown in FIG. 3A, in which the display area 230 shows a numerical cabin altimeter that presents a representation of cabin altitude 232 with a hatched rectangle 238 covering any leading blank spaces—which aids in the quick recognition of the digits by the pilot when low values are being displayed. The display area 230 also shows a mode indicator 234, which tells the pilot the selected display mode (which in the example shown is numerical altimeter mode). A simple status indicator 236a (which in this case is "OK") indicates that cabin altitude is acceptable. The situation-normal LED indicator 220 is illuminated with a cool color (such as green or blue), which also quickly informs the pilot that the cabin altitude is acceptable. Use of green or another cool color is typically associated by pilots with acceptable conditions and, therefore, a pilot will be quickly conditioned to recognize normal cabin altitude when this LED is illuminated.

Figure 3B:
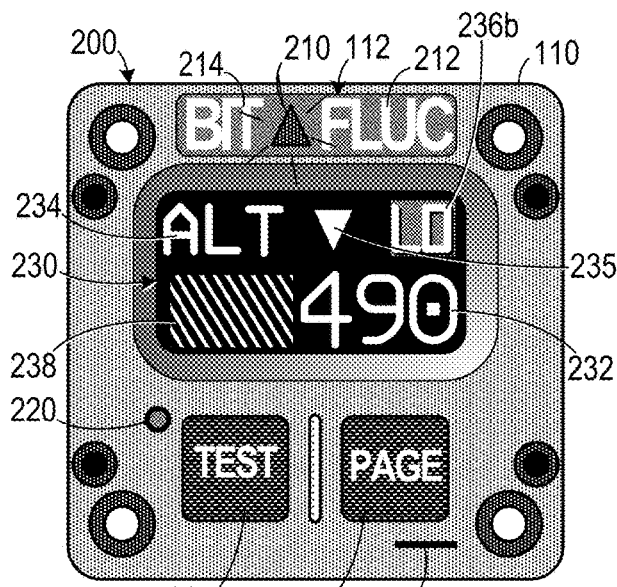

As shown in FIG. 3B, if the cabin altitude is below an acceptable range, a warning indicator 210 is illuminated with a warm color (such as red or orange) and LED 220 is turned off. The warning indicator 210 can be of a different shape (e.g., triangular) from that of the situation-normal LED indicator 220 (e.g., round) to further facilitate easy recognition of the different situations. Additionally, the status indicator 236b (which in this case is "LO") can provide a confirming indication that cabin altitude is below the desired range. The cabin altimeter 232 in this case shows a low number, which is made easier to recognize by the hatched rectangle 238 covering the leading blank area. A change indicator 235, which in this case is a downwardly-pointing triangle, indicates that the cabin altitude is decreasing. This situation could also be coupled with an audible alarm, which could further facilitate easy recognition by a pilot who might be experiencing hypoxia-related cognitive impairment.

Figure 3C:
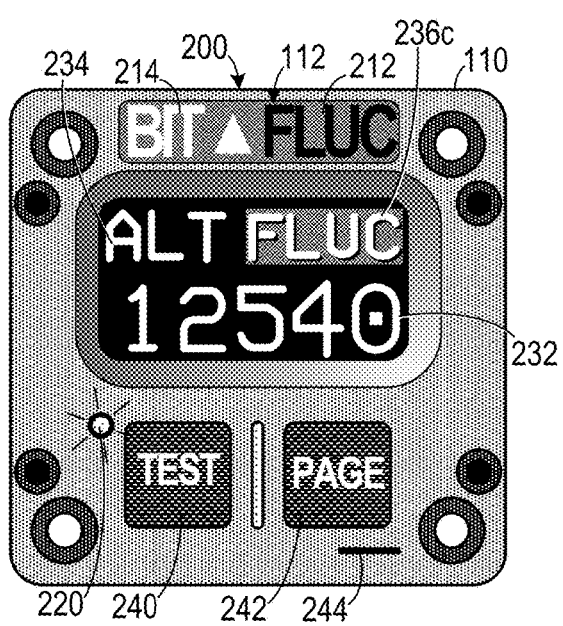

As shown in FIG. 3C, the status indicator 236*b* could indicate that the cabin altitude 232 is fluctuating, which can be a normal condition if the aircraft is performing certain maneuvers.

Figure 3D:
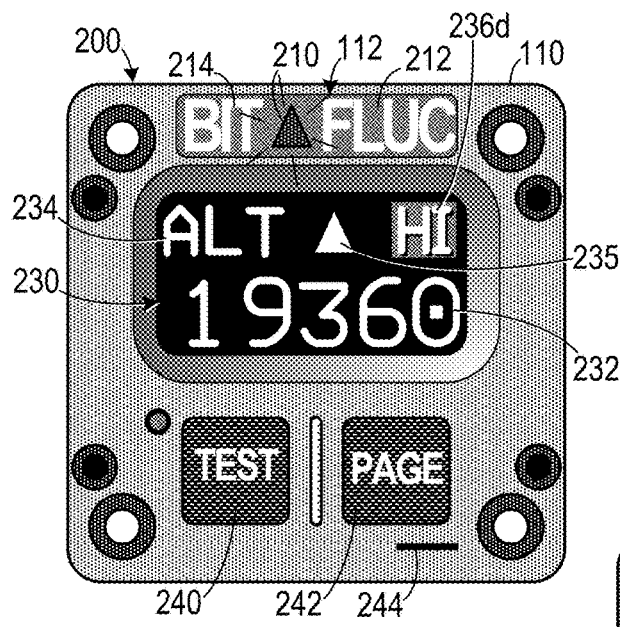

As shown in FIG. 3D, the cabin altitude 232 can be high, which is the situation that might indicate depressurization and can result in pilot hypoxia. In this case, status indicator 236*d* indicates that the cabin altitude is "HI" and the warning indicator 210 is illuminated. Because, warning indicator 210 is spaced apart from LED 220 and because warm colors (such as red) generally connote alarm conditions, the pilot is likely to recognize a potentially dangerous situation quickly, even though the pilot might already be experiencing some of the cognitive effects associated with hypoxia.

Figure 3E:
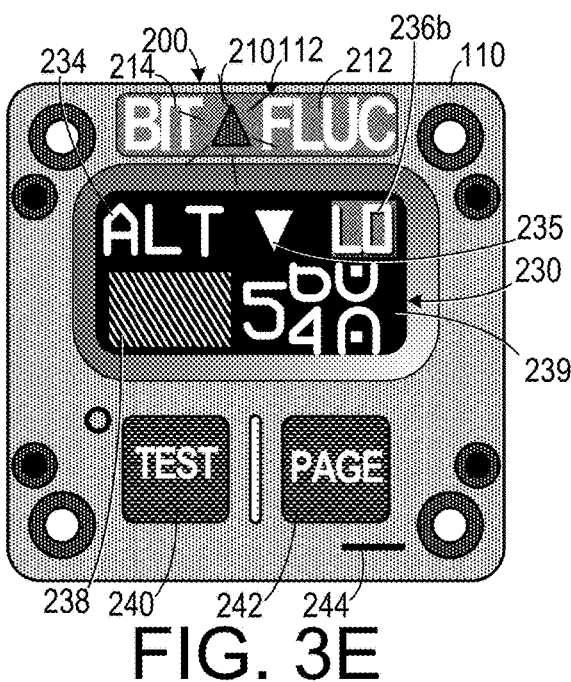
Figure 3F:
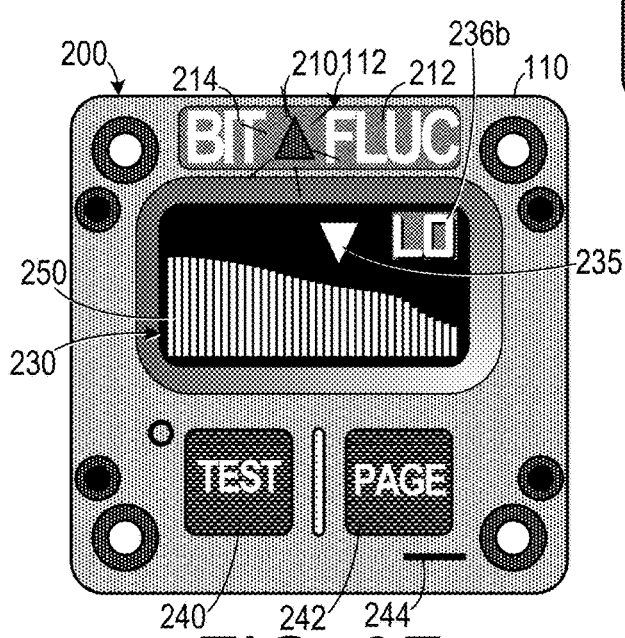

As shown in FIG. 3E, one of the display modes shows rolling digits 239 in the manner of an analog altimeter. As shown in FIG. 3F, one of the display modes shows a bar graph 250 of cabin altitude over time.

Figure 4A:
FIGS. 4A-4AQ are depictions of different display configurations employable with the present system.
Figure 4B:
Figure 4C:
Figure 4D:
Figure 4E:
Figure 4F:
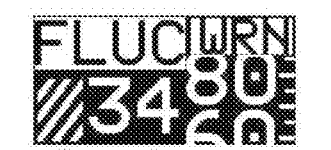
Figure 4G:
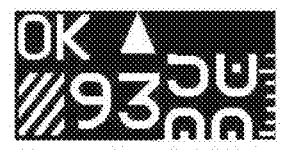
Figure 4H:
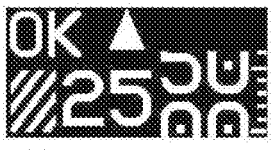
Figure 4I:
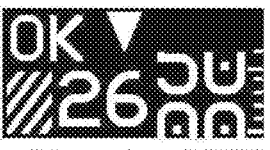
Figure 4J:
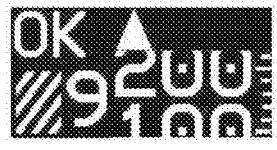
Figure 4K:
Figure 4L:
Figure 4M:
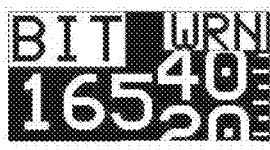
Figure 4N:
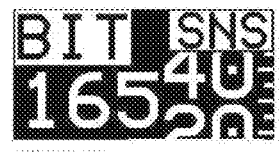
Figure 4O:
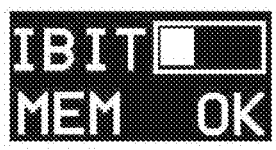
Figure 4P:
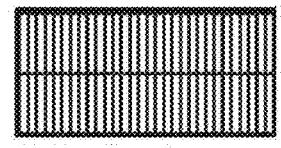
Figure 4Q:
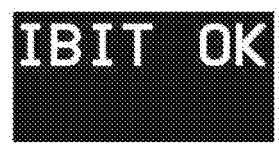
Figure 4R:
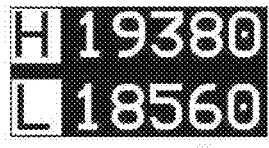
Figure 4S:
Figure 4T:
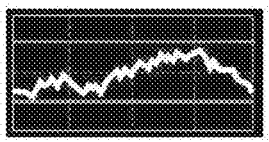
Figure 4U:
Figure 4V:
Figure 4W:
Figure 4X:
Figure 4Y:
Figure 4Z:
Figure 4A:
Figure 4A:
Figure 4A:
Figure 4A:
Figure 4A:
Figure 4A:
Figure 4A:
Figure 4A:
Figure 4A:
Figure 4A:
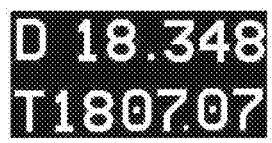

As shown in FIGS. 4A-4AQ, the display can have many different modes that can be selectable by the pilot and by technicians working on the system. While the displays are shown as white characters on a black background, in night mode they would typically be represented as green characters on a black background and in daylight mode they could be represented as black characters on a white background. The mode selection could be made manually by the pilot or automatically based on time/location or sensed ambient light. Also, in some embodiments, other colors could be selectable by the pilot or technician. The display can also have either a two row format, as shown in FIG. 5A, or a one row format, as shown in FIG. 5B.

Figure 6A:
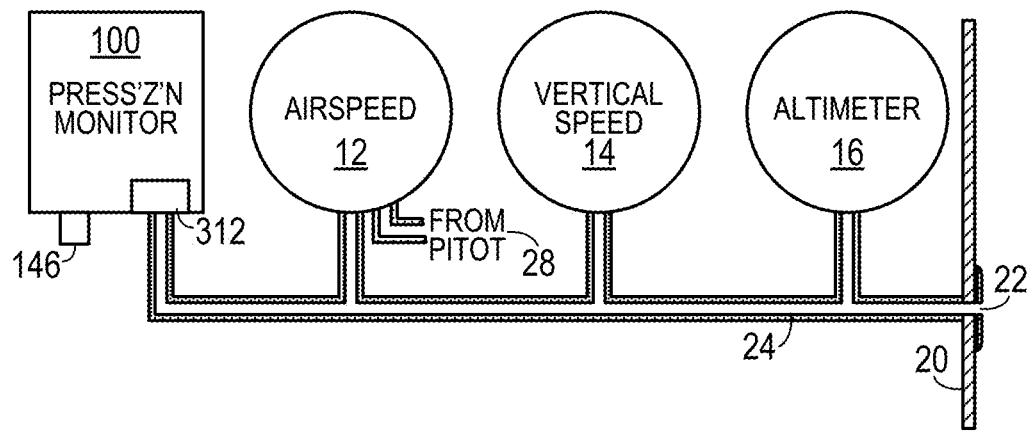
FIG. 6A is a schematic diagram showing a cockpit pressurization and oxygen warning system coupled to a static pressure line.
Figure 6B:
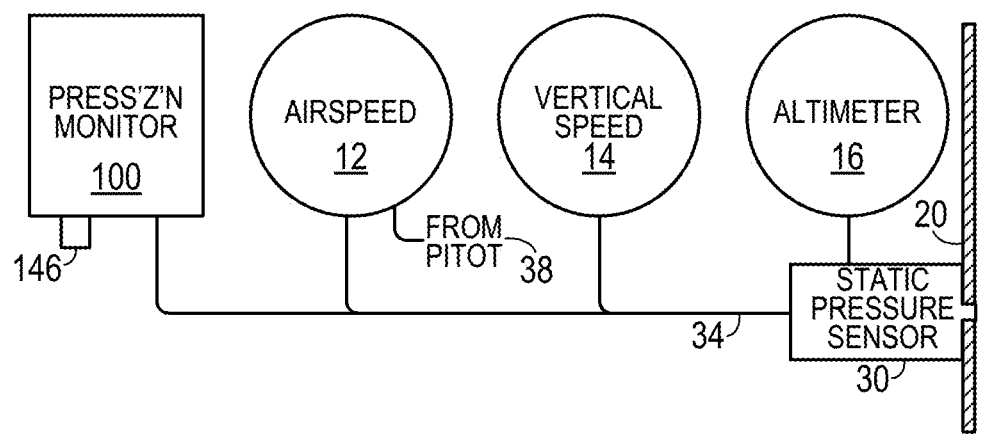
FIG. 6B is a schematic diagram showing a cockpit pressurization and oxygen warning system coupled to an electronic static pressure sensor.

As shown in FIG. 6A, the cockpit pressurization and oxygen warning system 100 can be configured to work with an aircraft having a standard static port 22 opening through the aircraft's skin 20 and coupled to a static pressure air line 24, to which is coupled such instruments as an airspeed indicator 12, a vertical speed indicator 14 and an altimeter 16. The warning system 100 receives a static pressure indication from the static pressure line 24 and a pressure transducer 312 converts the static pressure to an electronic signal representative thereof. An electronic pressure transducer 146 measures cabin pressure and generates an electronic signal representative thereof. If the aircraft employs a digital static pressure sensor 30, as shown in FIG. 6B, the warning system 100 receives a static pressure indication from a static pressure signal wire 34.

In one representative embodiment, the cockpit pressurization and oxygen warning system 100 can include the following components:

Cockpit Pressure Altimeter (CPA)
Displays and records data including altitude
OBOGS Concentrator Outlet Pressure Sensor (COPS)
Measures pressure of the OBOGS concentrator
Nose Wheel Well pressure sensor (NWW)
Provides altitude reference for CPA In one representative embodiment, the cockpit pressurization and oxygen warning system 100 can be configured into the following modes:

CPOMS 1—uses NWW sensor for altitude reference
CPA-101
COPS-103
NWW-105
CPOMS 2—uses FCC/ADC for altitude reference
CPA-101
COPS-103

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. An avionics interface device for presenting information to a pilot, comprising:
    (a) an avionics data input; and
    (b) a display device that presents a numerical representation of data from the avionics data input and that presents a hatched rectangular region immediately adjacent to and left of the numerical representation of data in substitution for any leading blank spaces that would otherwise be presented to the left of the numerical representation of data, thereby aiding in quick recognition of the numerical representation of data by the pilot when low values are being displayed,
    embodied in a cockpit pressurization monitoring apparatus and oxygen warning system in an aircraft flown by a pilot and having an aircraft altitude and a cabin altitude, wherein the avionics data input comprises a cabin pressure input and an aircraft pressure input and wherein the display device includes a pilot interface including a first visual indicator having a first recognizable characteristic disposed in a first position that is made visually perceptible when a first signal is asserted and a second visual indicator having a second recognizable characteristic aesthetically different from the first recognizable characteristic and disposed in a second position different from the first position that is made visually perceptible when a second signal is asserted, and further comprising a control circuit that is responsive to the cabin pressure input and the aircraft pressure input that determines an acceptable range for the cabin altitude that corresponds to the aircraft altitude and that determines the cabin altitude as a function of the cabin pressure input and that asserts the first signal only when the cabin altitude is within the acceptable range and not when the cabin altitude is not within the acceptable range, and that asserts the second signal only when the cabin altitude is not within the acceptable range and not when the cabin altitude is within the acceptable range.

2. The avionics interface device of claim 1, wherein the first visual indicator comprises a first light emitting device that emits light of a first color and wherein the second visual indicator comprises a second light emitting device that emits light of a second color that is different from the first color.

3. The avionics interface device of claim 1, wherein the first visual indicator comprises a first light emitting device that emits light in a first shape and wherein the second visual indicator comprises a second light emitting device that emits light in a second shape different from the first shape.

4. The avionics interface device of claim 3, wherein the first shape includes a circular shape and wherein the second shape includes a triangular shape.

5. An avionics interface device for presenting information to a pilot, comprising:
   (a) an avionics data input; and
   (b) a display device that presents a numerical representation of data from the avionics data input and that presents a hatched rectangular region immediately adjacent to and left of the numerical representation of data in substitution for any leading blank spaces that would otherwise be presented to the left of the numerical representation of data, thereby aiding in quick recognition of the numerical representation of data by the pilot when low values are being displayed, embodied in a cockpit pressurization monitoring apparatus and oxygen warning system in an aircraft flown by a pilot and having an aircraft altitude and a cabin altitude, wherein the avionics data input comprises a cabin pressure input and an aircraft pressure input and wherein the display device includes a pilot interface including a first visual indicator having a first recognizable characteristic disposed in a first position that is made visually perceptible when a first signal is asserted and a second visual indicator having a second recognizable characteristic aesthetically different from the first recognizable characteristic and disposed in a second position different from the first position that is made visually perceptible when a second signal is asserted, and further comprising a control circuit that is responsive to the cabin pressure input and the aircraft pressure input that determines an acceptable range for the cabin altitude that corresponds to the aircraft altitude and that determines the cabin altitude as a function of the cabin pressure input and that asserts the first signal only when the cabin altitude is within the acceptable range and not when the cabin altitude is not within the acceptable range, and that asserts the second signal only when the cabin altitude is not within the acceptable range and not when the cabin altitude is within the acceptable range, wherein the first visual indicator comprises a first light emitting device that emits light in a first shape and wherein the second visual indicator comprises a second light emitting device that emits light in a second shape different from the first shape.

6. The avionics interface device of claim 5, wherein the first visual indicator comprises a first light emitting device that emits light of a first color and wherein the second visual indicator comprises a second light emitting device that emits light of a second color that is different from the first color.

7. The avionics interface device of claim 5, wherein the first shape includes a circular shape and wherein the second shape includes a triangular shape.

* * * * *